United States Patent [19]
Nickell

[11] 3,994,715
[45] Nov. 30, 1976

[54] VANILLIN AS RIPENER FOR SUGARCANE
[75] Inventor: Louis G. Nickell, Honolulu, Hawaii
[73] Assignee: Hawaiian Sugar Planters' Association, Honolulu, Hawaii
[22] Filed: Apr. 17, 1975
[21] Appl. No.: 569,075

[52] U.S. Cl. .................................. 71/122; 71/76
[51] Int. Cl.² ................................. A01N 9/24
[58] Field of Search .................. 71/122, 123, 76

[56] References Cited
UNITED STATES PATENTS
2,775,613   12/1956   Garber .................................. 71/76 X OTHER PUBLICATIONS
Samuels et al., Chem. Abst., vol. 73, (1973) 39164s.
Georgiev et al., Chem. Abst., vol. 77, (1972) 122957c.
Pashkar et al., Chem. Abst., vol. 70, (1969) 76588p.
Singh et al., Chem. Abst., vol. 72, (1970) 30496v.

Primary Examiner—Lewis Gotts
Assistant Examiner—Catherine L. Mills
Attorney, Agent, or Firm—Burns, Doane, Swecker & Mathis

[57] ABSTRACT

Sucrose yield of sugarcane is increased by treating the cane crop a few weeks prior to harvest with a ripening agent comprising a hydroxy alkoxy substituted benzaldehyde or acetophephenone, such as vanillin, ethyl vanillin or acetovanillone, or with mixtures comprising one or more such compounds.

8 Claims, No Drawings

VANILLIN AS RIPENER FOR SUGARCANE

FIELD OF THE INVENTION

This invention relats to an improvement in the production of sugar from sugarcane. More particularly it relates to a process for increasing the sugar yield of sugarcane by applying vanillin or certain compounds related thereto to the maturing sugarcane plants in the field a few weeks prior to harvest. It also relates to compositions of matter useful for this purpose.

THE PRIOR ART

A number of chemical ripeners for sugarcane have been previously proposed. Some of these are disclosed, for example, in U.S. Pat. Nos. 3,224,865; 3,245,775; 3,291,592; 3,482,959; 3,482,961; 3,493,361; 3,505,056; 3,660,072 and 3,671,219. Still other chemical agents which have been found successful or shown promise as sugarcane ripeners, such as cyclo-leucine, anisomycin and cycloheximide, are disclosed, for instance, in Hawaiian Planters' Record, Vol. 58, No. 5, pp. 71–79 (1970). The use of still other compounds as sugarcane ripeners is disclosed and claimed by the present applicant in copending applications Ser. Nos. 455,954 and 455,955, both filed Mar. 28, 1974 now U.S. Pat. Nos. 3,897,240 and 3,897,239, respectively.

As previously stated, the more active ripeners differ widely from each other in terms of chemical structure as well as chemical and biological properties. In the search for effective ripeners failures continue to outnumber successes by a wide margin, and as of this date there is still no known screening test for determining the ripening activity of a compound other than to test it on maturing sugarcane. Moreover, because of toxicological or ecological concerns and the consequent possibility that rotation of use of different chemical ripeners in consecutive seasons in a given area may be preferable to the continued use of a single ripener or ripener mixture, the search for new sugarcane ripeners continues unabated.

OBJECTS OF THE INVENTION

It is an object of this invention to provide new and econimically useful chemical ripening agents for sugarcane. A more general object is to increase the sucrose yield of sugarcane by chemically treating it during its maturation prior to harvest without introducing objectionable toxicological hazards. More specifically, it is an object of this invention to increase the sucrose yield of maturing sugarcane by treating a cane crop nearing its normal harvest time with naturally occurring, relatively inexpensive compounds, or with synthetic equivalents or homologs thereof, which are sufficiently stable to provide the desired effect over a period of several weeks between application and a variable harvest date, but yet have a relatively low degree of persistence and are susceptible to autodecomposition or to decomposition by soil bacteria. Compounds which increase the sucrose content only temporarily over a period of three weeks or less after application and then result in a substantial decrease are usually not desirable chemical ripeners except in situations where harvesting time can be rigidly programmed in advance in relation to the time of application of the chemical ripener.

SUMMARY OF THE INVENTION

According to the present invention the sucrose yield of sugarcane is importantly increased by applying to the ripening cane crop a ripening composition comprising a lower alkoxysubstituted phenolic carbonyl compound corresponding to the formula

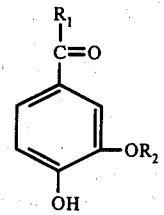

wherein $R_1$ stands for hydrogen or methyl and $R_2$ stands for the methyl or ethyl, or mixtures of two or more of the foregoing. More specifically, an excellent increase in sucrose yield has been obtained by applying a spray or dust comprising vanillin to maturing sugarcane stalks in a crop near the end of its normal maturation cycle, and harvesting such a crop some weeks later. Similar results may be obtained with related compounds such as ethyl vanillin or with acetovanillone. The composition is applied directly to the stalks by spraying, dusting or the like in order that it be deposited on the stalks including the younger, growing parts thereof. The normal maturation cycle of sugarcane under conditions such as those prevailing in Hawaii is from about 18 to about 36 months, though in some areas sugarcane is ripe and ready for harvest in 9 to 12 months.

The preferred usage form is a mixture containing the active compound in an aqueous solution or suspension utilizing one or a combination of known surface active agents commonly and variously used in the prior art as wetting agents, detergents or emulsifying agents. However, dry dusting compositions containing the vanillin compound and a solid diluent such as clay are also useful.

Vanillin, 4-hydroxy-3-methoxybenzaldehyde, is a well known compound which is present in small quantities in many natural plants, particularly the vanilla pod. It is also found in potato parings, in the sugar beet, and in balsams and other natural oils and resins. Vanillin can also be synthesized from guaiacol, from eugenol, from safrole and from lignin present in waste sulfite liquors. Vanillin is a white or slightly yellow crystalline solid having a melting point at 80°–81° C., is slightly soluble in water and freely soluble in solvents such as propylene glycol, ethanol, dimethyl ether, glacial acetic acid, chloroform, carbon disulfide, pyridine and in aqueous solutions of alkali metal hydroxides, e.g., sodium or potassium hydroxide. Pure vanillin is commonly used as a flavoring agent in the preparation of desserts and other foods, as well as a fixative in the manufacture of perfumes and the like. Vanillin has no appreciable physiological activity in the small amounts usually employed for flavoring. Certain hydrazones of vanillin are said to have a plant killing action similar to 2,4-D. See Reed et al, Compt. rend., 230, 2317–18 (1950).

Other alkoxy-substituted phenolic carbonyl compounds which may be used according to the present invention include ethyl vanillin (4-hydroxy-3-ethoxybenzaldehyde), which is commonly used as a flavoring or aromatic agent in place of vanillin, and acetovanillone (4-hydroxy-3-methoxyacetophenone). Acetonvanillone commonly occurs as an impurity (up to 3%) in vanillin as prepared from waste sulfite liquor. Crude vanillin containing a small amount, e.g., 1 to 3% by weight, of acetonvanillone is available commercially and may be used for the purposes of this invention.

The present discovery of the effective ripening activity of vanillin and certain of its related alkoxy-substituted phenolic carbonyl compounds is astonishing, as by contrast the corresponding benzoic acid (vanillic acid) is without activity as a sugarcane ripener.

In accordance with this invention, a sugarcane crop which is nearing the normal maturity stage, e.g., a crop in Hawaii which is 18 to 36 months of age, is treated with the alkoxysubstituted phenolic carbonyl compound, e.g., vanillin, or with a composition containing one or more of such compounds about two to ten weeks before harvest. The preferred time for such treatment is between about four and ten weeks prior to harvest.

Good results are obtained when the sugarcane crop is treated in the field at a rate in the range of from 1 to 4 pounds per acre (about 1 to 4 kilograms per hectare) of vanillin or equivalent. However, higher rates of chemical ripener, e.g., up to about 30 pounds per acre (30 kilograms per hectare) or more, or rates lower than 1 pound per acre (1 kilogram per hectare) can also be used. One hectare, it will be noted, is equal to 10,000 square meters. The optimum amount will vary somewhat depending on the particular mode of application, environmental conditions, time of year, and age and variety of cane being treated, but can be readily determined for each particular case by preliminary testing.

The active agent is conveniently applied in the field in the form of an aqueous solution, emulsion or suspension, i.e., in a liquid composition which may be sprayed onto the maturing cane plants from a boom-spray, or it can be dusted on from an airplane or the like as a dust composition which contains the active compound diluted with an inert solid such as clay.

In preparing suitable liquid compositions, surface active agents of the type described,, for instance, in U.S. Pat. No. 3,224,865, column 2, lines 61–66 or in U.S. Pat. No. 3,245,775, column 2, lines 57–64 are convenient to use. The preferred surfactants for use in liquid compositions of the present invention are those of the non-ionic type, e.g., alkyl phenoxy poly(ethylene-oxy) ethanols such as adducts of nonyl-phenol and ethylene oxide; trimethyl nonyl polyethylene glycol ethers; polyethylene oxide adducts of fatty and resin acids, and long chain alkyl mercaptan adducts with ethylene oxide.

With the type of boom-spray apparatus used in this work, it has been found convenient to apply the active ripener to the sugarcane field in the form of an aqueous solution, suspension or emulsion having a concentration of active agent such that the application at the rate of from 5 to 20 gallons per acre (about 45 to 200 liters per hectare) of liquid composition will provide the required dosage of active chemical. However, the use of lower or higher liquid volumetric rates may be preferred when a different dispensing mechanism is used.

The preferred carrier for the active ripening agent is water to which about 0.1 to 2% by weight of surface active agent has been added. However, instead of using water as the carrier, non-phytotoxic mineral oils either as such or in the form of water-in-oil or oil-in-water emulsions may be used similarly in accordance with practices which are otherwise well known in the art of treating vegetation in the field with beneficial growth control agents. Excellent results are obtained when the ripening agents of the present invention constitute essentially the sole active ingredients in the treating composition, but they may also be applied in combination with other agents.

DESCRIPTION OF SPECIFIC EMBODIMENTS

EXAMPLE 1

Part A - Preparation of Treating Composition

A treating composition is prepared by weighing out 1 gram of vanillin (U.S.P. grade) and dissolving it in approximately 6 ml of water. This mixture is diluted with water to exactly 8 ml, 1 drop of commercial Tergitol NPX (liquid) surfactant is added with a medicine dropper to the diluted vanillin mixture. The suspension is agitated by shaking prior to application.

Part B - Application of Vanillin Composition to Cane

A 0.3 ml dose of the aqueous suspension containing 38 mg vanillin, prepared as described in Part A above, was applied on the spindle area at the top of the last visible dewlap of each of a group of stalks of sugarcane in test plots in three different commercial cane fields in Hawaii at three different times of the year, using a syringe with a fine needle as a microapplicator.

Other groups of stalks in the same test plots were treated in an identical manner for comparative purposes with the same dosage of "Trysben" (dimethylamine salt of 2,3,6-trichlorobenzoic acid), used as a standard because of its known and consistent good activity; in one set of tests (Table IA) a group of stalks was also similarly treated with vanillic acid (4-hydroxy-3-methoxybenzoic acid).

The age of the cane at the time of application was 23.5 months in one of these field tests, 21.25 months in the other, and 23.75 months in the third field test.

A set of 10 of these treated stalks from each group of the three field tests were harvested four weeks after such treatment. A set of 10 untreated stalks from the same plots were also harvested at the same time as a control. In addition, in the second and third field tests another set of 10 stalks from each group were harvested five weeks after the time of the treatment.

The top 15 joints of each 10-stalk set of the treated stalks, as well as those of untreated control stalks from the same test plot, were removed, and each set was combined and analyzed in terms of juice purity and pol percent cane, following the so-called "press method" developed by T. Tanimoto, Hawaiian Planters' Record, 57, 133 (1964). "Pol percent cane" is a polarimetric determination and equals the percentage of sucrose if sucrose is the only optically active substance in the solution. In any event, determination of the pol percent cane is a standard and effective method for determining the sucrose content of sugarcane. The test results are given in Tables IA, IB and IC.

The data show that treatment with vanillin brings about a major increase in sucrose yield as compared with the untreated cane. Vanillin was found to be about as effective a ripener as the standard ripener, Trysben, under the conditions of the test reported in Table IA. In the test reported in Table IB vanillin was found to be considerably less effective than Trysben in the 4-week test but its relative effectiveness increased materially during the fifth week after treatment. In the test reported in Table IC neither vanillin nor Trysben showed any appreciable effect after four weeks but five weeks after treatment the stalks treated with vanillin contained about 33% more sucrose than the untreated stalks and materially more than the stalks treated with Trysben. The differences in results between the several series of tests are attributable to differences in atmospheric and other external conditions.

Vanillic acid was totally ineffective. See Table IA.

TABLE IA

| Cane Variety: | 49-3553 Field K |
|---|---|
| Age: | 23.5 months |
| Date of Treatment: | April 14, Year X |

| | Harvest Time After Treatment | |
|---|---|---|
| | 4 Weeks | |
| Ripening Agent | Juice Purity | Pol % Cane |
| Vanillin, 38 mg/stalk | 83.06 | 11.98 |
| Vanillic Acid, 38 mg/stalk | 74.65 | 8.78 |
| Trysben (standard) | 85.19 | 12.32 |
| None (control) | 76.94 | 9.77 |

EXAMPLE 2

In this example vanillin and Trysben, respectively, were applied to crops of sugarcane one year and two years after the tests reported in Example 1. In each case sets of treated and untreated cane stalks were again harvested and evaluated four weeks and five weeks after the date of treatment. The procedure and dosage used were the same as in Example 1. The test data are shown in Tables IIA and IIB below.

Tables IIA and IIB again show the beneficial ripening effect of vanillin on sugarcane during its maturation. In the test shown in Table IIA, wherein the cane was harvested in the winter season, the best results were obtained with vanillin when the cane was harvested five weeks after treatment. On the other hand, in the test shown in Table IIB, where the cane was harvested in the spring, a better sucrose yield was obtained four weeks after treatment than five weeks after treatment.

While the foregoing data were obtained using pure vanillin as the ripening agent, similar results can be achieved using either crude vanillin (containing 1 to 3% acetovanillone or ethyl vanillin or acetovanillone itself.

TABLE IIA

| Cane Variety: | 50-7209 Field N |
|---|---|
| Age: | 18.75 months |
| Date of Treatment: | November 16, Year X + 1 |
| Dates of Harvest: | December 14 and December 21, Year X + 1 |

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Vanillin, 38 mg/stalk | 62.01 | 6.71 | 71.71 | 8.81 |
| Trysben (standard) | 65.94 | 8.84 | 67.61 | 8.48 |
| None (control) | 61.77 | 7.91 | 62.83 | 6.13 |

TABLE IB

| Cane Variety: | 50-7209 Field L |
|---|---|
| Age: | 21.25 months |
| Date of Treatment: | August 4, Year X |

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Vanillin, 38 mg/stalk | 66.33 | 6.51 | 75.09 | 8.63 |
| Trysben (standard) | 83.30 | 11.66 | 84.64 | 12.44 |
| None (control) | 61.15 | 5.64 | 64.10 | 6.87 |

TABLE IC

| Cane Variety: | 50-7209 Field M |
|---|---|
| Age: | 23.75 months |
| Date of Treatment: | October 13, Year X |

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Vanillin, 38 mg/stalk | 67.55 | 7.54 | 78.91 | 10.19 |
| Trysben (standard) | 67.84 | 7.65 | 78.83 | 9.55 |
| None (control) | 67.97 | 7.72 | 70.40 | 7.70 |

TABLE IIB

| Cane Variety: | 59-3775 Field O |
|---|---|
| Age | 18.75 month |
| Date of Treatment: | April 3, Year X + 2 |
| Dates of Harvest: | May 1 and May 7, Year X + 2 |

| | Harvest Time After Treatment | | | |
|---|---|---|---|---|
| | 4 Weeks | | 5 Weeks | |
| Ripening Agent | Juice Purity | Pol % Cane | Juice Purity | Pol % Cane |
| Vanillin, 38 mg/stalk | 75.33 | 8.81 | 69.94 | 7.56 |
| Trysben (standard) | 74.38 | 9.72 | 73.75 | 9.07 |
| None (control) | 69.73 | 7.70 | 70.57 | 6.83 |

The nature, scope, utility and effectiveness of the present invention have been described and exemplified in the foregoing specification. However, these examples are not intended to be limiting. The true scope of the invention which is to be protected by patent is particularly pointed out in the appended claims.

What is claimed is:

1. A process for modifying the ripening of field grown sugarcane plants so as to increase their yield of sucrose which comprises applying to the cane plants at a time from 2 to 10 weeks prior to harvest and when the plants are 9 to 36 months of age a sucrose increasing amount of a ripening agent which is selected from the group consisting of vanillin, ethyl vanillin and acetovanillone.

2. A process according to claim 1 wherein said ripening agent is sprayed onto the cane plants as a liquid composition containing water as a carrier.

3. A process according to claim 2 wherein the aqueous composition contains between 0.1 and 2% by weight of a surface active agent.

4. A process according to claim 2 wherein the aqueous composition contains between 0.1 and 2% by weight of a nonionic surface active agent.

5. A process for modifying the ripening of field grown sugarcane plants so as to increase their yield of sucrose which comprises applying a sucrose increasing amount of vanillin to the cane plants at a time from 2 to 10 weeks prior to harvest and when the plants are between 9 and 36 months of age.

6. A process according to claim 5 wherein said vanillin is applied to the cane plants at the rate of about 1 to 4 pounds per acre.

7. A process according to claim 1 wherein said ripening agent is ethyl vanillin.

8. A process according to claim 1 wherein said ripening agent is acetovanillone.

* * * * *